United States Patent
Hirose et al.

(10) Patent No.: US 8,299,303 B2
(45) Date of Patent: Oct. 30, 2012

(54) PROCESS FOR PRODUCING A CONCENTRATED SOLUTION FOR A PHOTORESIST-STRIPPING LIQUID HAVING LOW WATER CONTENT

(75) Inventors: Katsutoshi Hirose, Hyogo (JP); Hiroya Koyama, Hyogo (JP); Kimihiro Kamasaka, Hyogo (JP); Taro Sasabe, Hyogo (JP); Naoshi Kai, Hyogo (JP)

(73) Assignee: KNC Laboratories Co., Ltd., Hyogo (JP)

(*) Notice: Subject to any disclaimer, the term of this patent is extended or adjusted under 35 U.S.C. 154(b) by 232 days.

(21) Appl. No.: 12/863,841

(22) PCT Filed: Aug. 27, 2009

(86) PCT No.: PCT/JP2009/004169
§ 371 (c)(1),
(2), (4) Date: Jul. 21, 2010

(87) PCT Pub. No.: WO2010/073430
PCT Pub. Date: Jul. 1, 2010

(65) Prior Publication Data
US 2010/0298605 A1    Nov. 25, 2010

(30) Foreign Application Priority Data
Dec. 26, 2008 (JP) ................. 2008-332084

(51) Int. Cl.
C07C 211/62 (2006.01)
C07C 211/63 (2006.01)
C07C 209/82 (2006.01)

(52) U.S. Cl. .................................... 564/296

(58) Field of Classification Search ............ 564/296
See application file for complete search history.

(56) References Cited

U.S. PATENT DOCUMENTS

| | | |
|---|---|---|
| 5,185,235 A | 2/1993 | Sato et al. |
| 5,252,257 A | 10/1993 | Hoffmann et al. |
| 7,268,256 B2 * | 9/2007 | Kikuyama et al. ............ 564/296 |

FOREIGN PATENT DOCUMENTS

| | | |
|---|---|---|
| JP | 59-134752 | 8/1984 |
| JP | 01-158444 | 6/1989 |
| JP | 04-338366 | 11/1992 |
| WO | 2007/053363 | 5/2007 |
| WO | 2008/051627 | 5/2008 |

OTHER PUBLICATIONS

International Preliminary Report on Patentability and Written Opinion of the International Searching Authority issued Aug. 25, 2011 in International (PCT) Application No. PCT/JP2009/004169.
International Search Report issued Nov. 24, 2009 in International (PCT) Application No. PCT/JP2009/004169.

* cited by examiner

*Primary Examiner* — Brian J Davis
(74) *Attorney, Agent, or Firm* — Wenderoth, Lind & Ponack, L.L.P.

(57) ABSTRACT

There is provided a process for producing a concentrated solution of quaternary ammonium hydroxide which is characterized in that quaternary ammonium hydroxide in a form of water-containing crystals or of an aqueous solution is mixed with a water-soluble organic solvent selected from the group consisting of glycol ether, glycol and triol and the resulting mixed solution is subjected to a thin-film distillation in vacuo so as to evaporate the low boiling material. In accordance with this process, a concentrated solution of quaternary ammonium hydroxide having low water content is able to be easily produced.

10 Claims, No Drawings

PROCESS FOR PRODUCING A CONCENTRATED SOLUTION FOR A PHOTORESIST-STRIPPING LIQUID HAVING LOW WATER CONTENT

TECHNICAL FIELD OF THE INVENTION

The present invention relates to a process for producing a concentrated solution of quaternary ammonium hydroxide which is used as a material for a photoresist-stripping liquid and, more particularly, it relates to a process for producing a concentrated solution of quaternary ammonium hydroxide having lower water content than the conventional ones.

BACKGROUND ART

In the manufacture of liquid crystal panel elements and semiconductor elements such as IC and LSI, a chemically vapor-deposited (CVD) electroconductive metal film and an insulating film such as $SiO_2$ film are firstly prepared on a substrate such as silicon wafer or glass. After that, a photoresist is uniformly applied on the electroconductive metal film and the insulating film and then selectively exposed to light and developed to form a resist pattern. Then the substrate is selectively subjected to a dry etching process using the resist pattern as a mask whereupon a fine circuit is formed. After that, photoresist film residue and etching residue which are no longer necessary are washed and removed using a stripping liquid.

Although some stripping effects are achieved when an aqueous solution of sodium hydroxide or a common organic solvent is used solely as the stripping liquid, the resulting stripping effect is not sufficient. Accordingly, various stripping liquids for the photoresist have been proposed already for enhancing the stripping property. One of the common methods among them is a method where a solution of quaternary ammonium hydroxide such as tetramethylammonium hydroxide (TMAH) is used.

In that method, preparation of a stripping liquid is usually carried out in such a manner that a solution prepared from commercially available water-containing crystals of quaternary ammonium hydroxide or a commercially available aqueous solution of quaternary ammonium hydroxide is diluted with an organic solvent such as dimethyl sulfoxide (DMSO) or 3-methoxy-3-methyl-1-butanol (MMB) down to a desired concentration.

On the other hand, it has been known that the stripping property of a stripping liquid is also dependent upon the amount of water contained in the stripping liquid and that the lower the water content, the higher the stripping property. Since a stripping liquid is prepared by diluting a quaternary ammonium hydroxide solution with an organic solvent as mentioned above, it is necessary for lowering the water content in the stripping liquid that a quaternary ammonium hydroxide solution is concentrated so as to make the water content therein low.

With regard to a method for concentrating a quaternary ammonium hydroxide solution to make the water content low, there is a known method whereby a pentahydrate of TMAH (ratio by weight of TMAH to water is 1:1) is dissolved in methanol and concentrated in vacuo according to a batch system and also a method whereby a DMSO solution containing TMAH pentahydrate is dried by adding molecular sieves thereto (please see Patent Documents 1 and 2).

However, in the former method, there are disadvantages that heating for long time is necessary whereby TMAH is apt to be decomposed and that, since the product obtained after the concentration is a solid, its handling is difficult. On the other hand, in the latter method, there are disadvantages that, due to the use of molecular sieves, the cost is high and the operation is complicated. Further, since the presence of fine particles in the concentrated solution and in the stripping liquid is not preferred, there is a disadvantage that the molecular sieves must be removed after drying. Furthermore, the water content in the concentrated solution prepared by such a method is not satisfactorily low. Accordingly, the conventional process for producing a concentrated solution of quaternary ammonium hydroxide still needs to be improved.

REFERENCES

Patent Document 1: WO 2007/053363
Patent Document 2: WO 2008/051627

DISCLOSURE OF THE INVENTION

Problem that the Invention is to Solve

The present invention has been achieved in view of the current status of the prior art as such and an object thereof is to provide a process by which a concentrated solution of quaternary ammonium hydroxide having low water content is able to be easily produced.

Means for Solving the Problem

In order to achieve the above object, the present inventors have carried out extensive investigations in the manufacturing conditions for producing a concentrated solution of quaternary ammonium hydroxide having low water content and, as a result, they have found that, when quaternary ammonium hydroxide in a form of water-containing crystals or of an aqueous solution is mixed with a specific water-soluble organic solvent followed by subjecting to a thin-film distillation, a concentrated solution of quaternary ammonium hydroxide having low water content is able to be produced whereupon the present invention has been achieved.

Thus, in accordance with the present invention, there is provided a process for producing a concentrated solution of quaternary ammonium hydroxide which is characterized in that quaternary ammonium hydroxide in a form of water-containing crystals or of an aqueous solution is mixed with a water-soluble organic solvent selected from the group consisting of glycol ether, glycol and triol and the resulting mixed solution is subjected to a thin-film distillation in vacuo so as to evaporate the low boiling material.

Further, in accordance with the present invention, there is also provided a concentrated solution of quaternary ammonium hydroxide produced by the above-mentioned production process which is characterized in that the drying coefficient (DC) defined by the following formula is not less than 3.5.

$$\text{Drying Coefficient } (DC) = \frac{\text{quaternary ammonium hydroxide in a concentrated solution (\% by weight)}}{\text{water in a concentrated solution (\% by weight)}}$$

Advantages of the Invention

In accordance with the production process of the present invention, a concentrated solution of quaternary ammonium hydroxide having low water content is able to be easily produced merely by such a manner that the quaternary ammonium hydroxide in a form of water-containing crystals or of an aqueous solution is mixed with a specific water-soluble organic solvent followed by subjecting to a thin-film distillation. In addition, the concentrated solution produced as such is able to achieve a low water content (a high drying coefficient of not less than 3.5) as compared with the concentrated solution produced by the conventionally known production process. Accordingly, when it is used as a stripping liquid for photoresist, very high stripping effect is able to be expected. Further, since a thin-film distillation is used in the production process of the present invention, a quaternary ammonium hydroxide solution is able to be concentrated by means of heating within a short period of time, whereby decomposition of the quaternary ammonium hydroxide during the concentrating operation rarely happens. Still further, since the product obtained by the concentrating operation is a liquid, its handling is easy.

BEST MODE FOR CARRYING OUT THE INVENTION

As hereunder, the production process of the present invention will be more specifically illustrated. The production process in accordance with the present invention is characterized in that quaternary ammonium hydroxide in a form of water-containing crystals or of an aqueous solution is mixed with a specific water-soluble organic solvent followed by subjecting to a thin-film distillation.

With regard to the quaternary ammonium hydroxide, there may be used a hydroxide of quaternary ammonium such as tetramethylammonium hydroxide, tetraethylammonium hydroxide, tetrapropylammonium hydroxide, tetrabutylammonium hydroxide, trimethylethylammonium hydroxide, dimethyldiethylammonium hydroxide, trimethyl(2-hydroxyethyl)ammonium hydroxide, and triethyl (2-hydroxyethyl) ammonium hydroxide, as well as a hydroxide of bipyrrolidinium such as spiro-[1,1']-bipyrrolidinium hydroxide. Among them, tetramethylammonium hydroxide (TMAH), tetrapropylammonium hydroxide, and spiro-[1,1']-bipyrrolidinium hydroxide are preferred in view of enhancement of the stripping property and TMAH is particularly preferred. Incidentally, the quaternary ammonium hydroxide may be used solely or two or more thereof may be used jointly.

The quaternary ammonium hydroxide is used in a form of water-containing crystals or of an aqueous solution. Although any of those forms gives a good result in the production process of the present invention, it is preferred, when the quaternary ammonium hydroxide is TMAH, to use an aqueous solution of TMAH in view of the cost since water-containing crystals of TMAH (TMAH pentahydrate) are considerably expensive as compared with an aqueous solution of TMAH (a 25% by weight of aqueous solution of TMAH).

In the production process of the present invention, the quaternary ammonium hydroxide is mixed with a water-soluble organic solvent selected from the group consisting of glycol ether, glycol and triol. Examples of the glycol ether which is able to be used in the present invention include ethylene glycol monomethyl ether, ethylene glycol monoethyl ether, ethylene glycol monobutyl ether, diethylene glycol monomethyl ether, diethylene glycol monoethyl ether, diethylene glycol monopropyl ether, diethylene glycol monobutyl ether, triethylene glycol monomethyl ether, 3-methoxy-3-methyl-1-butanol, dipropylene glycol monomethyl ether, and 2-(2-methoxyethoxy)ethanol. Examples of the glycol include ethylene glycol, propylene glycol, diethylene glycol, dipropylene glycol, and triethylene glycol. Example of the triol includes glycerin. Among them, 3-methoxy-3-methyl-1-butanol (MMB), diethylene glycol, propylene glycol, glycerin and 2-(2-methoxyethoxy)ethanol are preferred, and when the solvent used for the manufacture of the stripping liquid by diluting the concentrated solution is MMB, then MMB is particularly preferred in view of its affinity for the solvent.

Although the reason why these water-soluble organic solvents are effective for lowering the water content in quaternary ammonium hydroxide in the production process of the present invention has not been fully clarified yet, it is likely that, since any of glycol ether, glycol and triol is an alcohol and is a protic polar solvent, quaternary ammonium hydroxide is stabilized thereby and its decomposition is retarded.

In the production process of the present invention, there is no particular limitation for the compounding ratio by weight of the quaternary ammonium hydroxide to the water-soluble organic solvent and, although the ratio may be able to be appropriately set up depending upon the aimed concentration of the quaternary ammonium hydroxide in the stripping liquid which is to be manufactured at last, it is usually from about 1:0.5 to about 1:30.

When the quaternary ammonium hydroxide is mixed with the water-soluble organic solvent, an alkanolamine may be further added thereto. When an alkanolamine is mixed therewith, the mixed solution of the quaternary ammonium hydroxide with the water-soluble organic solvent is able to be made uniform. Moreover, when an alkanolamine is mixed therewith, the water-soluble organic solvent is able to be removed much more during the thin-film distillation. Examples of the alkanolamine which is used in the present invention include monoethanolamine (MEA), diethanolamine, triethanolamine, ethylaminoethanol, dimethylaminoethanol, diethylaminoethanol, 2-(2-aminoethoxy)ethanol and the like. Among them, monoethanolamine and 2-(2-aminoethoxy)ethanol are preferably used. Each of them may be used solely or two or more thereof may be used jointly. Although there is no particular limitation for the amount of the alkanolamine used therefor, it is usually up to about 20% by weight to the total amount of the 25% quaternary ammonium hydroxide and the water-soluble organic solvent.

In the production method of the present invention, the quaternary ammonium hydroxide is mixed with the water-soluble organic solvent together, if desired, with the alkanolamine and the resulting mixed solution is subjected to a thin-film distillation in vacuo so as to evaporate the low boiling material as mentioned above. Such an operation is able to be easily carried out using the commercially available thin-film distillation device. There is no particular limitation for the distilling temperature and the vacuum degree and, for example, they may be from 80° C. to 130° C. and from 0.1 kPa to 5.0 kPa, respectively.

The residue after the distillation obtained by the above production process of the present invention is a concentrated solution of quaternary ammonium hydroxide of the present invention. The concentrated solution has a DC (drying coefficient) of not less than 3.5 or not less than 4.0 or, particularly, not less than 5.0 and is a concentrated solution containing very low amount of water therein. Accordingly, when this concentrated solution is used, a stripping liquid for photoresist having a very high stripping property is able to be prepared. Incidentally, although the upper limit of the DC of the concentrated solution is not particularly limited in a theoretical view, it may be, for example, not more than 50 or not more than 30 or, particularly, not more than 15.

EXAMPLES

Hereinafter, the present invention will be further explained by using the Examples although these Examples are mere illustrations for explaining the present invention and the present invention is not limited thereto.

In the Examples, KDL5 or KD10 which are short path distilling devices (hereinafter, they will be abbreviated as SPD) manufactured by UIC, Germany was used.

Amount of TMAH or amount of TMAH and MEA (in case MEA is used) in the distilled residue was calculated by means of a neutralization titration. Amount of water (water content) was calculated using a Karl-Fischer aquameter. Amount of the water-soluble organic solvent was calculated by deducting the amount of TMAH or amount of TMAH and MEA (in case MEA is used) and the amount of water from the weight of the distilled residue.

Comparative Example

As a material for the distillation, 32.0 g of 25% by weight of aqueous solution of TMAH and 80.0 g of DMSO were mixed and a thin-film distillation was carried out using SPD (KDL5) as a thin-film distilling device where the distilling temperature was 100° C. and the vacuum degree was 1.1 kPa to evaporate the low boiling material. When the residue after the distillation (a concentrated solution of quaternary ammonium hydroxide) was analyzed, it contained 3.9 g of TMAH, 21.8 g of DMSO and 2.1 g of water (TMAH:DMSO:water=14.1% by weight:78.2% by weight:7.7% by weight) (DC=1.8). Crystals immediately separated out from the residue after the distillation.

Example 1

As a material for the distillation, 12.0 g of 25% by weight of aqueous solution of TMAH and 60.0 g of propylene glycol were mixed and a thin-film distillation was carried out using SPD (KDL5) as a thin-film distilling device where the distilling temperature was 100° C. and the vacuum degree was 1.9 kPa to evaporate the low boiling material. When the residue after the distillation (a concentrated solution of quaternary ammonium hydroxide) was analyzed, it contained 2.5 g of TMAH, 17.0 g of propylene glycol and 0.4 g of water (TMAH:propylene glycol:water=12.6% by weight:85.4% by weight:2.0% by weight) (DC=6.3). No crystals were found in the residue after the distillation.

Example 2

As a material for the distillation, 21.1 g of 25% by weight of aqueous solution of TMAH and 63.3 g of diethylene glycol were mixed and a thin-film distillation was carried out using SPD (KDL5) as a thin-film distilling device where the distilling temperature was 100° C. and the vacuum degree was 1.7 kPa to evaporate the low boiling material. When the residue after the distillation (a concentrated solution of quaternary ammonium hydroxide) was analyzed, it contained 4.9 g of TMAH, 49.4 g of diethylene glycol and 0.6 g of water (TMAH:diethylene glycol:water=8.9% by weight:90.0% by weight:1.1% by weight) (DC=8.1). No crystals were found in the residue after the distillation.

Example 3

As a material for the distillation, 20.1 g of 25% by weight of aqueous solution of TMAH and 60.3 g of 2-(2-methoxyethoxy)ethanol were mixed and a thin-film distillation was carried out using SPD (KDL5) as a thin-film distilling device where the distilling temperature was 100° C. and the vacuum degree was 1.9 kPa to evaporate the low boiling material. When the residue after the distillation (a concentrated solution of quaternary ammonium hydroxide) was analyzed, it contained 4.5 g of TMAH, 22.9 g of 2-(2-methoxyethoxy)ethanol and 1.1 g of water (TMAH:2-(2-methoxyethoxy)ethanol:water=15.8% by weight:80.2% by weight:4.0% by weight) (DC=4.0). No crystals were found in the residue after the distillation.

Example 4

As a material for the distillation, 12.0 g of 25% by weight of aqueous solution of TMAH and 60.0 g of MMB were mixed and a thin-film distillation was carried out using SPD (KDL5) as a thin-film distilling device where the distilling temperature was 100° C. and the vacuum degree was 1.7 kPa to evaporate the low boiling material. When the residue after the distillation (a concentrated solution of quaternary ammonium hydroxide) was analyzed, it contained 2.0 g of TMAH, 9.9 g of MMB and 0.4 g of water (TMAH:MMB:water=16.0% by weight:80.8% by weight:3.1% by weight) (DC=5.1). No crystals were found in the residue after the distillation.

Example 5

As a material for the distillation, 7.96 kg of 25% by weight of aqueous solution of TMAH, 16.0 kg of MMB and 1.2 kg of MEA were mixed and a thin-film distillation was carried out using SPD (KD10) as a thin-film distilling device where the distilling temperature was 100° C. and the vacuum degree was 1.7 kPa to evaporate the low boiling material. When the residue after the distillation (a concentrated solution of quaternary ammonium hydroxide) was analyzed, it contained 1.68 kg of TMAH, 6.5 kg of MMB, 0.60 kg of MEA, and 0.26 kg of water (TMAH:MMB:MEA:water=18.6% by weight:71.9% by weight:6.6% by weight:2.9% by weight) (DC=6.5). No crystals were found in the residue after the distillation.

Example 6

As a material for the distillation, 6.2 g of TMAH pentahydrate and 49.6 g of MMB were mixed and a thin-film distillation was carried out using SPD (KDL5) as a thin-film distilling device where the distilling temperature was 100° C. and the vacuum degree was 1.9 kPa to evaporate the low boiling material. When the residue after the distillation (a concentrated solution of quaternary ammonium hydroxide) was analyzed, it contained 2.4 g of TMAH, 11.5 g of MMB and 0.5 g of water (TMAH:MMB:water=17.0% by weight:79.5% by weight:3.5% by weight) (DC=4.9). Some crystals separated out in the residue after the distillation.

Example 7

As a material for the distillation, 50.4 g of 25% by weight of aqueous solution of TMAH and 50.4 g of glycerin were mixed and a thin-film distillation was carried out using SPD (KDL5) as a thin-film distilling device where the distilling temperature was 100° C. and the vacuum degree was 1.6 kPa to evaporate the low boiling material. When the residue after the distillation (a concentrated solution of quaternary ammonium hydroxide) was analyzed, it contained 10.6 g of TMAH, 39.7 g of glycerin and 0.8 g of water (TMAH:glycerin:water=20.7% by weight:77.8% by weight:1.5% by weight) (DC=13.8). No crystals were found in the residue after the distillation.

Materials used in Comparative Example and Examples to 7 and drying coefficients (DC) of the resulting concentrated solutions prepared therein are shown in the following Table 1.

TABLE 1

| | Comparative Example | Example 1 | Example 2 | Example 3 | Example 4 | Example 5 | Example 6 | Example 7 |
|---|---|---|---|---|---|---|---|---|
| Quaternary ammonium hydroxide | 25% by weight of aqueous solution of TMAH | 25% by weight of aqueous solution of TMAH | 25% by weight of aqueous solution of TMAH | 25% by weight of aqueous solution of TMAH | 25% by weight of aqueous solution of TMAH | 25% by weight of aqueous solution of TMAH | TMAH pentahydrate | 25% by weight of aqueous solution of TMAH |
| Water-soluble organic solvent | DMSO | propylene glycol | diethylene glycol | 2-(2-methoxyethoxy)ethanol | MMB | MMB | MMB | glycerin |
| Alkanolamine | — | — | — | — | — | MEA | — | — |
| Drying coefficient of the resulting concentrated solution | 1.8 | 6.3 | 8.1 | 4.0 | 5.1 | 6.5 | 4.9 | 13.8 |

It will be apparent from Table 1 that, in Comparative Example where DMSO was used as a water-soluble organic solvent, only the concentrated solution having a low DC (1.8) was produced while, in any of Examples 1 to 7 where glycol ether (MMB, 2-(2-methoxyethoxy)ethanol), glycol (diethylene glycol, propylene glycol) or triol (glycerin) was used as a water-soluble organic solvent, the concentrated solution having DC of not lower than 3.5 was produced. From the result as such, it is apparent that, when quaternary ammonium hydroxide in a form of water-containing crystals or of an aqueous solution is mixed with glycol ether, glycol or triol followed by subjecting to a thin-film distillation, a concentrated solution having low water content is able to be produced.

INDUSTRIAL APPLICABILITY

The production process in accordance with the present invention is able to produce a concentrated solution of quaternary ammonium hydroxide having low water content which has been unable to be achieved by the conventionally known production processes and, accordingly, the process is very useful for producing a concentrated solution for the material of a photoresist-stripping liquid having a high stripping property.

The invention claimed is:

1. A process for producing a concentrated solution of a quaternary ammonium hydroxide comprising:
   mixing a quaternary ammonium hydroxide in a form of water-containing crystals, or an aqueous solution of a quaternary ammonium hydroxide, with a water-soluble organic solvent selected from the group consisting of a glycol ether, a glycol and a triol, to obtain a mixed solution; and
   subjecting the resulting mixed solution to a thin-film distillation in vacuo so as to evaporate the low boiling material.

2. The production process according to claim 1, wherein the quaternary ammonium hydroxide is tetramethylammonium hydroxide, and the tetramethylammonium hydroxide is in a form of an aqueous solution.

3. The production process according to claim 1, wherein the water-soluble organic solvent is 3-methoxy-3-methyl-1-butanol, diethylene glycol, propylene glycol, glycerin, or 2-(2-methoxyethoxy)ethanol.

4. The production process according to claim 3, wherein the water-soluble organic solvent is 3-methoxy-3-methyl-1-butanol.

5. The production process according to claim 1, further comprising mixing an alkanolamine with the mixed solution.

6. A concentrated solution of a quaternary ammonium hydroxide produced by the production process according to claim 1, wherein the drying coefficient (DC) defined by the following formula is not less than 3.5:

$$\text{Drying Coefficient }(DC) = \frac{\text{quaternary ammonium hydroxide in a concentrated solution (\% by weight)}}{\text{water in a concentrated solution (\% by weight)}}.$$

7. A concentrated solution of a quaternary ammonium hydroxide produced by the production process according to claim 2, wherein the drying coefficient (DC) defined by the following formula is not less than 3.5:

$$\text{Drying Coefficient }(DC) = \frac{\text{quaternary ammonium hydroxide in a concentrated solution (\% by weight)}}{\text{water in a concentrated solution (\% by weight)}}.$$

8. A concentrated solution of a quaternary ammonium hydroxide produced by the production process according to claim 3, wherein the drying coefficient (DC) defined by the following formula is not less than 3.5:

$$\text{Drying Coefficient }(DC) = \frac{\text{quaternary ammonium hydroxide in a concentrated solution (\% by weight)}}{\text{water in a concentrated solution (\% by weight)}}.$$

9. A concentrated solution of a quaternary ammonium hydroxide produced by the production process according to claim 4, wherein the drying coefficient (DC) defined by the following formula is not less than 3.5:

$$\text{Drying Coefficient } (DC) = \frac{\text{quaternary ammonium hydroxide in a concentrated solution (\% by weight)}}{\text{water in a concentrated solution (\% by weight)}}.$$

10. A concentrated solution of a quaternary ammonium hydroxide produced by the production process according to claim 5, wherein the drying coefficient (DC) defined by the following formula is not less than 3.5:

$$\text{Drying Coefficient } (DC) = \frac{\text{quaternary ammonium hydroxide in a concentrated solution (\% by weight)}}{\text{water in a concentrated solution (\% by weight)}}.$$

* * * * *